United States Patent [19]
Walworth

[11] 3,981,717
[45] Sept. 21, 1976

[54] HERBICIDAL METHODS

[75] Inventor: Bryant Leonidas Walworth, Pennington, N.J.

[73] Assignee: American Cyanamid Company, Stamford, Conn.

[22] Filed: Sept. 24, 1969

[21] Appl. No.: 860,796

[52] U.S. Cl. ................................ 71/105; 71/111; 260/465 D; 260/471 A
[51] Int. Cl.² ........................................ A01N 9/20
[58] Field of Search .............. 71/105, 108, 111, 121

[56] References Cited
UNITED STATES PATENTS

| | | | |
|---|---|---|---|
| 2,412,510 | 12/1946 | Jones | 71/118 |
| 2,726,945 | 12/1955 | Heininger | 71/105 |
| 3,656,932 | 4/1972 | Scheuermann et al. | 71/105 |

*Primary Examiner*—Glennon H. Hollrah
*Attorney, Agent, or Firm*—H. G. Jackson

[57] ABSTRACT

Herbicidal methods employing anilino compounds having the formula:

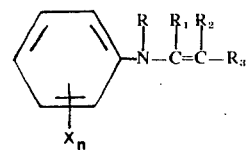

wherein R and $R_1$ are selected from the group consisting of hydrogen and methyl; $R_2$ and $R_3$ are selected from the group consisting of CN and COOY, where Y is an alkyl group having from 1 to 8 carbon atoms; X is selected from the group consisting of lower alkyl having 1 to 4 carbon atoms, lower alkoxy having from 1 to 4 carbon atoms, nitro, trifluoromethyl, and halo; and $n$ is an integer from 0 to 2, are disclosed.

9 Claims, No Drawings

HERBICIDAL METHODS

The present invention relates to anilino compounds which are useful as herbicides. It further relates to herbicidal compositions and methods of controlling growth of undesirable plants.

The anilino compounds of this invention are represented by the formula:

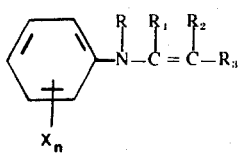

wherein R and $R_1$ are selected from the group consisting of hydrogen and methyl; $R_2$ and $R_3$ are selected from the group consisting of CN and COOY, where Y is an alkyl group having from 1 to 8 carbon atoms such as methyl, ethyl, propyl, isopropyl, n-butyl, tertiary butyl, n-amyl, the normal and branched hexyls, heptyls and octyls; X is selected from the groups consisting of lower alkyl having from 1 to 4 carbon atoms such as methyl, ethyl, propyl, isopropyl, n-butyl, tertiary butyl; lower alkoxy having from 1 to 4 carbon atoms, such as methoxy, ethoxy, propoxy, isopropoxy, n-butoxy, tertiary butoxy, halo, such as fluoro, chloro, bromo and iodo, nitro; and trifluoromethyl; and $n$ is an integer of from 0 to 2.

PREPARATION

The compounds of Formula I are prepared by a reaction of an aromatic amine, orthoformate or orthoacetate and an active methylene compound in accordance with the following equation. The ingredients may be heated together with or without a solvent.

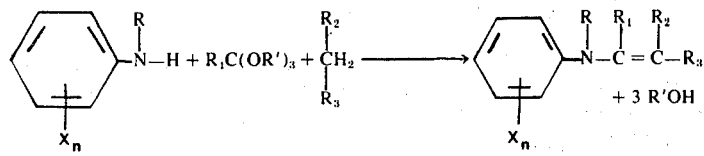

wherein R' is a lower alkyl group having from 1 to 4 carbon atoms and X, $n$, R, $R_1$, $R_2$ and $R_3$ are as defined above.

Suitable primary aromatic amines include, for example, the following known compounds:
aniline
2-methylaniline
2-ethoxyaniline
2-butoxyaniline
2-hydroxyaniline
2-($\alpha,\alpha,\alpha$-trifluoromethyl)aniline
3-methylaniline
3-chloroaniline
4-nitroaniline
4-hydroxyaniline
4-methoxyaniline
4-nitroaniline
4-chloroaniline
4-n-butylaniline
2,4-dichloroaniline
2-propoxy-5-nitroaniline
2-methoxy-5-chloroaniline
2,6-diethylaniline
2,6-dimethoxyaniline
2-chloro-6-hydroxyaniline
3,4-dibromoaniline Also useful are the corresponding N-methyl aromatic amines. They are prepared by means of standard alkylation reactions such as those disclosed in *Synthetic Organic Chemistry*, R. B. Wagner, H. D. Zook, John Wiley and Sons, Inc., page 666 (1953) and references cited therein. Suitable N-methyl aromatic amines include, for example:
N-methylaniline
N-methyl-2-methylaniline
N-methyl-2-ethoxyaniline
N-methyl-2-butoxyaniline
N-methyl-2-hydroxyaniline
N-methyl-2-($\alpha,\alpha,\alpha$-trifluoromethyl)aniline
N-methyl-3-methylaniline
N-methyl-3-chloroaniline
N-methyl-3-fluoroaniline
N-methyl-4-nitroaniline
N-methyl-4-hydroxyaniline
N-methyl-4-methoxyaniline
N-methyl-4-nitroaniline
N-methyl-4-chloroaniline
N-methyl-4-n-butylaniline
N-methyl-2,4-dichloroaniline
N-methyl-2-propoxy-5-nitroaniline
N-methyl-2-methoxy-5-chloroaniline
N-methyl-2,6-diethylaniline
N-methyl-2,6-dimethoxyaniline
N-methyl-2-chloro-6-hydroxyaniline
N-methyl-3,4-dibromoaniline Illustrative of suitable known orthoformates and orthoacetates are trimethoxymethane, triethoxymethane, triisopropoxymethane, triisobutoxymethane, 1,1,1-trimethoxyethane and 1,1,1-triethoxyethane.

The following known compounds are illustrative of suitable active methylene containing compounds: dimethyl malonate, diethyl malonate, dibutyl malonate, di-n-octyl malonate, methyl ethyl malonate, ethyl isopropyl malonate, malononitrile, ethyl cyanoacetate, isopropyl cyanoacetate, n-butyl cyanoacetate, n-hexyl cyanoacetate, n-heptyl cyanoacetate and n-octyl cyanoacetate.

COMPOSITIONS AND APPLICATION

The substituted anilino compounds of this invention exhibit a broad range of contact, postemergence herbicidal activity as well as preemergence activity. They may be formulated as solids or liquids and directly applied to the foliage of the growing plants or incorporated in the soil in which the plants are growing. Field application can be by such conventional techniques, as with powder dusters, boom and hand sprayers, spray dusters, addition to irrigation water and the like.

The toxicants are generally initially formulated as concentrated compositions, comprising the active ingredient and a solid or liquid adjuvant. The adjuvant serves as a formulation aid or conditioning agent, permitting the concentrates to be further mixed with a suitable solid or liquid carrier, in a form which enables prompt assimilation by plant systems.

Useful liquid adjuvants in which the toxicant is dissolved, suspended or distributed include, for example, the following organic solvents and mixtures thereof: hexane, benzene, toluene, acetone, cyclohexanone, methyl ethyl ketone, isopropanol, butanediol, methanol, xylene, dioxane, isopropyl ether, ethylene dichloride, tetrachloroethane, hydrogenated naphthalene, solvent naphtha, and petroleum fractions, such as, kerosene.

Useful solid adjuvants in which the toxicant is adsorbed or dispersed on or in include, for example: natural clays, such as china clays, bentonites and attapulgites; other natural materials, such as, talc, pyrophyllite, quartz, diatomaceous earth, fuller's earth, chalk, rock phosphate, kaolin, kieselguhr volcanic ash, salt and sulfur; chemically modified materials, such as acid washed bentonite, precipitated calcium phosphate, precipitated calcium carbonate, calcined magnesia, and colloidal silica; and other solid materials such as powdered cork, powdered wood and powdered pecan or walnut shells. For maximum adsorption and ease of handling, these materials are used in finely divided form of particles which range in size of from 20 to 40 mesh (tyler) or finer.

Prior to field application, the solid and liquid concentrate compositions are generally diluted by the addition of solid or liquid carriers. Suitable solid carriers, with which the concentrate compositions are mixed or adsorbed on or in, include: the previously mentioned solid adjuvants; fertilizers, such as, ammonium nitrate, urea, superphosphate, compost, manure and humus; pesticides; other herbicides; sand and the like. Suitable liquid carriers with which the concentrate compositions are dissolved, suspended, emulsified or dispersed include, for example, water and the liquid adjuvants previously mentioned.

Where solid concentrates are employed with liquid carriers they are advantageously employed in the form of powders made wettable by the addition of from about 1% to about 5% by weight of a dispersant, such as, a sodium salt of a high molecular weight carboxylic or sulfonic acid and about 1% to about 5% by weight of a wetting agent, such as, sodium oleylisethionate, lauryltrimethylammonium chloride, sodium lignin sulfate, etc. Three representative formulations are presented in Table I.

TABLE I

| Formulation Number | Ingredients | Weight Percent |
|---|---|---|
| I | ethyl 2-cyano-3-(N-methylanilino)-acrylate | 25 |
| | attapulgite | 71 |
| | naphthalene sulfonic acid condensate[1] | 2 |
| | sodium N-methyl-N-oleoyl taurate | 2 |

TABLE I-continued

| Formulation Number | Ingredients | Weight Percent |
|---|---|---|
| II | methyl 2-cyano-3-(N-methylanilino)-acrylate | 50 |
| | attapulgite | 45 |
| | sodium lignin sulfonate[2] | 3 |
| | sodium oleylisethionate[3] | 2 |
| III | octyl 2-cyano-3-(N-methylanilino)-acrylate | 75 |
| | diatomaceous earth | 20 |
| | naphthalene sulfonic acid condensate | 3 |
| | sodium oleylisethionate | 2 |

[1]Aerosol OS, American Cyanamid Company
[2]Marasperse N, Marathon Corporation
[3]Igepon A, Antara Chemicals Corporation Dusts are usually prepared by grinding together from about 2% to about 25% by weight of the active ingredient with a solid adjuvant and solid carrier. In preparing dust concentrates the active ingredient is added in from about 25% to about 90% concentrations.

Emulsifiable concentrates can be prepared by dissolving the active ingredient (about 25% to about 75% by weight) in an organic solvent, such as, acetone, methylisobutylketone, cyclohexanone, xylene or toluene and an emulsifier (about 1% to 10% by weight), such as, Mal 77L, by Wm. Cooper and Nephers or a 1:1 mixture of nonionic Toximul R and anionic Toximul S by Ninol Laboratories, Inc. and optionally a surfactant (about 1% to about 5%), such as, sodium lignin sulfonate. A representative formulation is presented in Table II.

TABLE II

| Formulation Number | Ingredients | Weight Percent |
|---|---|---|
| IV | ethyl 2-cyano-3-(N-methylanilino)-acrylate | 25 |
| | cyclohexanone | 65 |
| | Toximul R, Toximul S (equal parts) | 10 |

In general, control of undesirable plant species is achieved by field applications in which the active ingredient is applied in from about 0.5 to about 25 pounds per acre. The preferred range is from about 1 to about 10 pounds per acre.

This invention is further illustrated by the examples which appear below. Unless otherwise specified, parts and percentages are by weight.

EXAMPLE 1

Preparation of Ethyl 2-Cyano-3-(N-Methylanilino)acrylate

A mixture of N-methylaniline (214 g., 2.00 moles), triethylorthoformate (296 g., 1.99 moles) and ethyl cyanoacetate (2.26 g., 2.00 moles) are heated under reflux until the temperature of the reaction mixture reaches 165°C. The reaction vessel is then fitted for distillation and heated for an additional period of 30 minutes. 320 Ml. of distillate are removed.

The reaction mixture is diluted with 500 ml. of ethanol and treated hot with activated charcoal. The charcoal is removed by filtration. The desired crystalline product separates from solution upon cooling. It is collected by filtration, washed with diethyl ether and dried. The product weighs 224 g. (49% theoretical yield). Its melting point after recrystallization from ethanol is 101°–102°C.

EXAMPLE 2

Preparation of (1-p-Anisidinoethylidene)Malononitrile

A mixture of triethyl orthoformate (29.6 g., 0.20 mole), 4-methoxyaniline (24.6 g., 0.20 mole) and malononitrile (13.2 g., 0.20 mole) in 250 ml. of ethanol are heated under reflux for 3 hours. The desired crystalline product separates on cooling. It is isolated by filtration and washed with ethanol. Recrystallization from equal parts of ethanol and acetone gives 28.5 g. of product having a melting point of 254°–255°C.

EXAMPLES 3–29

The following compounds are prepared by the general procedures set forth in the foregoing examples:

3. Ethyl 3-anilino-2-cyanocrotonate
4. Ethyl 2-cyano-3-(N-methyl-p-anisidino)acrylate
5. Diethyl (N-methyl-p-anisidinomethylene)malonate
6. (N-methyl-p-anisidinomethylene)malononitrile
7. (1-anilinoethylidene)malononitrile
8. (N-methylanilinomethylene)malononitrile
9. Diethyl (anilinomethylene)malonate
10. Ethyl 2-cyano-3-(N-methylanilino)crotonate
11. Ethyl 2-cyano-3-(2,6-diethylanilino)acrylate
12. n-Butyl 2-cyano-3-(N-methyl-2-methylanilino)acrylate
13. Diethyl (2-ethoxyanilinomethylene)malonate
14. (N-methyl-2-butoxyanilinomethylene)malononitrile
15. 1-(2-hydroxyanilino)malononitrile
16. Ethyl 2-cyano-3-[N-methyl-2-($\alpha,\alpha,\alpha$-trifluoromethyl)-anilino]acrylate
17. Ethyl 2-cyano-3-(3-methylanilino)acrylate
18. Diethyl (3-chloroanilinomethylene)malonate
19. Ethyl 2-cyano-3-(N-methyl-4-nitroanilino)acrylate
20. Ethyl 2-cyano-3-(4-hydroxyanilino)acrylate
21. (1-p-nitroanilinoethylidene)malononitrile
22. (1-p-chloroanilinoethylidene)malononitrile
23. (N-methyl-4-n-butylanilinomethylene)malononitrile
24. Diethyl (2,4-dichloroanilinomethylene)malonate
25. (N-methyl-2-propoxy-5-nitroanilinoethylidene)-malononitrile
26. Ethyl 2-cyano-3-(2-methoxy-5-chloroanilino)acrylate
27. n-Octyl 2-cyano-3-(2,6-dimethoxyanilino)crotonate
28. (2-chloro-6-hydroxyanilinoethylidene)malononitrile
29. Ethyl 2-cyano-3-(2,4-dibromoanilino)acrylate

EXAMPLE 30

Postemergence Herbicidal Activity

The postemergence herbicidal activity of the compounds of the present invention is demonstrated by the following tests wherein a variety of monocotyledonous and dicotyledonous plants are treated with test compounds dispersed in aqueous-acetone mixtures. In the tests seedling plants are grown in jiffy flats for about two weeks. The test compounds are dispersed in 50/50 acetone/water mixtures in sufficient quantity to provide the equivalent of about 0.5 to 10 pounds per acre of active compound when applied to the plants through a spray nozzle operating at 30 p.s.i. for a predetermined time. After spraying, the plants are placed on greenhouse benches and are cared for by conventional greenhouse practices. Two weeks after treatment, the seedling plants are examined and rated according to the Herbitoxicity Index provided below. The data obtained are reported in Table III using the plant abbreviations listed below.

| Numerical Scale | Herbitoxicity Index Herbicidal Activity |
|---|---|
| 9 | 100% reduction in stand |
| 4– | 1-2 stunted plants remaining |
| 8 | 85–100% reduction in stand |
| 7 | 70–85% reduction in stand |
| 6 | 60–70% reduction in stand |
| 5 | 50–60% reduction in stand |
| 4 | 40–50% reduction in stand |
| 3 | 30–40% reduction in stand |
| 2 | 20–30% reduction in stand |
| 1 | 10–20% reduction in stand |
| 0 | no apparent effect |

| Abbreviation | Herbicidal Activity |
|---|---|
| s | severe injury |
| m | moderate injury |
| t | trace to slight injury |
| c | chlorosis |
| g | growth retarded |
| a | abnormal growth |
| r | regrowth |
| – | no test |

| Abreviation | Plant Abbreviations Common Name | Genus-Specie |
|---|---|---|
| AW | Alligator weed-*Alternanthera philoxeroides* | |
| BW | Field bindweed-*Convolvulus arvensis* | |
| CT | Canada thistle-*Cirsium arvense* | |
| DG | Dogfennel-*Anthemis cotula* | |
| JG | Johnsongrass-*Sorghum halepense* | |
| NS | Nutsedge-*Cyperus rotundus* | |
| QG | Quackgrass-*Agropyron repens* | |
| KO | Kochia-*Kochia scoparia* | |
| LA | Lambsquarter-*Chenopodium album* | |
| MU | Mustard-*Brassica kaber* | |
| PI | Pigweed-*Amaranthus retroflexus* | |
| BA | Barnyardgrass-*Echinochloa crusgalli* | |
| CR | Crabgrass-*Digitaria sanguinalis* | |
| GRF | Green foxtail-*Setaria viridis* | |
| WO | Wild oats-*Avena fatua* | |
| MI | Millet-*Setaria italica* | |
| PF | Parrot's feather-*Myriophyllum brasiliense* | |
| COR | Corn-*Zea mays* | |
| COT | Cotton-*Gossypium hirsutum* | |
| SOY | Soybean-*Glycine max* | |
| SB | Sugar beets-*Beta vulgaris* | |
| TO | Tomato-*Lycopersicon esculentum* | |
| WH | Wheat-*Triticum aestivum* | |
| RA | Radish-*Raphanus sativus* | |
| LB | Lima beans-*Phaseolus lunatus* | |
| SG | Sorghum-*Sorghum vulgare* | |
| CG | Cheatgrass-*Bromus secalinus* | |
| RG | Ryegrass-*Rolium multifluorum* | |
| PU | Purslane-*Portulaca oleracea* | |
| CW | Carpetweed-*Mollugo verticillata* | |
| GT | Giant foxtail-*Setaria faberii* | |

TABLE III

| Test Compound | Treatment LB/A | Perennial Weeds | | | | | | Annual Weeds | | | | | | | | | | | |
|---|---|---|---|---|---|---|---|---|---|---|---|---|---|---|---|---|---|---|
| | | AW | BW | CT | JG | NS | QG | KO | LA | MU | PI | PU | CG | BA | CR | GRF | WO | MI | RG |
| Ethyl 2-cyano-3-(N-methylanilino)-acrylate | 10 | | 9 | 9 | 0 | 0 | 0 | | 9 | 9 | 9 | | 9 | | 0 | 9 | 9 | 9 | 9 |
| | 2 | | 9 | 9 | 0 | 0 | 0 | | 9 | 9 | 7 | 9 | 9 | 9 | 0 | 0 | 5 | 5 | 9 |
| | .5 | | 0 | 0 | | | | | 9– | 3 | s | 9– | | 0 | | | | | |
| Methyl 2-cyano-3-(N-methylanilino)-acrylate | 10 | 9 | t | 9 | t | 0 | t | 9 | 9 | 9 | 9 | | | t | t | 9– | 9– | | |
| | 2 | m | 0 | t | t | 0 | 0 | 9– | 9 | t | 9 | | | t | t | m | 3 | | |
| n-Octyl 2-cyano-3-(N-methylanilino)-acrylate | 9 | | | | | | | 9 | 9 | 9 | 9 | | | 5 | 9 | 9 | 3 | | |
| | 3 | | | | | | | 8 | 9 | 9 | 9 | | | 7 | 9 | 9 | t | | |
| Ethyl 2-cyano-3-(N-methyl-3-chloro-anilino)acrylate | 10 | | 9 | 9 | 0 | 0 | 0 | | 9 | 9 | 9– | | | | 0 | | 5 | 9– | |
| | 2 | | 9 | 9 | 0 | 0 | 0 | | 7 | 9 | 9– | | | | 0 | | 0 | 5 | |
| Ethyl 2-cyano-3-(N-methyl-3-methyl-anilino)acrylate | 4 | | | | | | | | 9 | 9– | 9 | | | | s | | s | 3 | |
| | 1.5 | | | | | | | | 9 | 9 | 9– | | | | 3 | | 0 | 5 | |
| Ethyl 2-cyano-3-(N-methyl-2-methyl-anilino)acrylate | 4 | | | | | | | | 9 | 9 | 9– | | | | 0 | | s | s | |
| | 1.5 | | | | | | | | 9 | 5 | 9– | | | | 0 | | 0 | 0 | |

| Test Compound | Treatment LB/A | Crops | | | | | | |
|---|---|---|---|---|---|---|---|---|
| | | COR | COT | SOY | SB | TO | WH | RA |
| Ethyl 2-cyano-3-(N-methylanilino)-acrylate | 10 | | | | | 9 | 5 | 9 |
| | 2 | t | 0 | s | | | | |
| | .5 | 0 | 0 | 0 | | 0 | | |
| Methyl 2-cyano-3-(N-methylanilino)-acrylate | 10 | | | | | | | |
| | 2 | | | | | | | |
| n-Octyl 2-cyano-3-(N-methylanilino)-acrylate | 9 | | | | | | | |
| | 3 | 5m | s | t | | 9– | | |
| Ethyl 2-cyano-3-(N-methyl-3-chloro-anilino)acrylate | 10 | | | | | | | |
| | 2 | | | | | | | |
| Ethyl 2-cyano-3-(N-methyl-3-methyl-anilino)acrylate | 4 | | | | | | | |
| | 1.5 | | | | | | | |
| Ethyl 2-cyano-3-(N-methyl-2-methyl-anilino)acrylate | 4 | | | | | | | |
| | 1.5 | | | | | | | |

EXAMPLE 31

Selective Preemergence Herbicidal Activity

The selective preemergence herbicidal activity of the compounds of the invention is exemplified by the following tests in which the seeds of a variety of monocotyledonous and dicotyledonous plants are separately mixed with potting soil and planted on top of approximately one inch of potting soil in separate pint cups. After planting, the cups are sprayed with the selected aqueous-acetone solution containing test compound, in sufficient quantity to provide the equivalent of about 1.00 to 25 pounds per acre of test compound per cup. The treated cups are then placed on greenhouse benches and cared for in accordance with conventional greenhouse procedures. Three weeks after treatment, the tests are terminated and each cup is examined and rated according to the Herbitoxicity Index set forth in the previous example. The tabulated results of these tests establish the herbicidal proficiency of the test compounds and are reported in Table IV below.

TABLE IV

| Test Compound | Treatment LB/A | Annual Weeds | | | | | | | | | | | Crops | | | | | | |
|---|---|---|---|---|---|---|---|---|---|---|---|---|---|---|---|---|---|---|---|
| | | KO | LA | MU | PI | PU | CG | BA | CR | GRF | WO | MI | COR | COT | SOY | SB | TO | WH | RA |
| Ethyl 2-cyano-3-(N-methylanilino)-acrylate | 10 | 9– | 9 | 9 | 9 | 9 | 9 | 7 | 9 | 9 | 9– | | | | | | | | |
| | 4 | 3 | 9 | 9 | 7 | 9 | | 9– | 5 | 9 | 3 | 5 | mg | 0 | 7 | 9 | 9 | | |
| | 1 | 3 | 9 | 7 | t | 9 | 9 | 3 | 0 | 8 | t | 3 | 0 | 0 | t | 7 | | m | 9– |
| Methyl 2-cyano-3-(N-methylanilino)-acrylate | 25 | | | 9 | | | | | | | | | | | | | | 9– | 9– |
| | 4 | 0 | mg | 0 | 0 | | | sg | tg | 8 | 0 | | 0 | 0 | 0 | 5 | | | |
| Ethyl 2-cyano-3-(N-methyl-3-chloro-anilino)acrylate | 10 | | 9 | 9 | 9 | | | | 9– | 9– | | m | | | | | | | |
| | 2 | | s | 9 | s | | | | 5 | 9– | | 0 | | | | | | | |
| Ethyl 2-cyano-3-(N-methyl-3-methyl-anilino)acrylate | 4 | | 9 | 9 | 0 | | | | m | 0 | | 3 | | | | | | | |
| | 2 | | 0 | 0 | 0 | | | | 0 | 0 | | 0 | | | | | | | |
| Ethyl 2-cyano-3-N-methyl-2-methyl-anilino)acrylate | 4 | | 9 | 3 | 9 | | | | 9– | 0 | | 9 | | | | | | | |
| | 2 | | 7 | 0 | 3 | | | | 0 | 0 | | 0 | | | | | | | |
| Ethyl 2-cyano-3-(2,6-diethyl-anilino)acrylate | 7.5 | ta | 9a | 0 | 0 | | | 0 | 5 | 3 | 0 | | | | | | | | |

EXAMPLE 32

Postemergence Herbicidal Activity

The postemergence herbicidal activity of the compounds of the invention is further demonstrated by the following tests. The test compounds were dissolved in mixture containing 65% acetone and 35% water and applied to a variety of vigorously growing monocotyledonous and dicotyledonous seedling plants in sufficient amount to provide the equivalent of from about 4 to about 10 lbs. of the test compound per acre. The sprayed plants were placed on greenhouse benches to dry and cared for using conventional greenhouse practices. The effects on plant growth were determined after 14 days. The results according to the following Herbitoxicity Index are presented in Table V.

| Numerical Scale | Herbitoxicity Index |
|---|---|
| 0 | no observed effect |
| 0+ | trace injury |
| 1 | slight injury |
| 2 | moderate injury |
| 3 | severe injury, no kill |
| 4 | severe injury, <75% kill |
| 4+ | severe injury 75-90% kill |
| 5- | 90-99% kill |
| 5 | 100% kill |

TABLE V

| Compound | Rate LB/Acre | Perennial Weeds | | | | | Annual Weeds | | | | | | | Crops | | |
|---|---|---|---|---|---|---|---|---|---|---|---|---|---|---|---|---|
| | | AW | BW | CT | JG | QG | LA | MU | PI | BA | CR | WO | MI | TO | WH | RA |
| Ethyl 2-cyano-3-(N-methylanilino)acrylate | 10 | | | 5 | | | | 5 | | | | | | 5 | 5 | 5 |
| Methyl 2-cyano-3-(N-methylanilino)acrylate | 10 | | 5 | 1 | | 0 | | | | | 5 | | | 5 | 1 | 0 |
| n-Octyl 2-cyano-3-(N-methylanilino)acrylate | 10 | | 5 | 0 | 0 | 0 | | | | | 5 | | | 5 | 0 | 5 |
| Ethyl 2-cyano-3-(N-methyl-3-chloroanilino)acrylate | 10 | | 5 | 5 | 0 | 0 | 5 | 5 | 5- | | 0 | 4 | 5- | | | |
| Ethyl 2-cyano-3-(N-methyl-3-methylanilino)acrylate | 4 | | 5 | 5 | 0 | 0 | 5 | 5- | 5 | | .2 | 3 | 3+ | | | |
| Ethyl 2-cyano-3-(N-methyl-2-methylanilino)acrylate | 4 | | 5 | 5 | 0 | 0 | 5 | 5 | 5- | | 0 | 3 | 3 | | | |
| Ethyl 2-cyano-3-(N-methyl-4-hydroxyanilino)acrylate | 10 | | | | | | 5- | 5 | 1 | 1 | 1 | 1 | | 5 | 1 | 3 |
| Ethyl 2-cyano-3-methyl-3-(N-methylanilino)acrylate | 10 | | | | | | 4+ | 3 | 0 | 0 | | 0 | | 5 | 0 | 3 |

EXAMPLE 33

Premergence Herbicidal Activity

The preemergence herbicidal activity of the compounds of the present invention is demonstrated by the following tests. The test compounds are dissolved in 65% acetone, 35% water mixture and applied, through a spray nozzle operating at 30 p.s.i., to cups of potting soil in which a variety of monocotyledonous and dicotyledonous seedlings had been planted. The cups were placed in a greenhouse and cared for in accordance with conventional greenhouse procedure. After 21 days the cups were examined and rated according to the Herbitoxicity Index set forth in Example 32. The results are presented in Table VI.

TABLE VI

| Compound | Rate LB/Acre | Annual Weeds | | | | | | | | | | | | Crops | | | |
|---|---|---|---|---|---|---|---|---|---|---|---|---|---|---|---|---|---|
| | | LA | MU | PI | PU | CW | CG | GT | BA | CR | GRF | WO | MI | COR | RG | WH | RA | PA |
| Ethyl 2-cyano-3-(N-methyl-anilino)acrylate | 10 | | 5 | 5 | 5 | | 5 | | | 4+ | | 5 | 5- | | | | | |
| | 2 | | 5 | 5 | 5 | | 5- | | | 1 | | 3 | 3 | | | | | |
| Methyl 2-cyano-3-(N-methyl-anilino)acrylate | 25 | | | | | | | | | | | 5 | | 5 | 5 | 5- | | |
| Ethyl 2-cyano-3-(N-methyl-3-chloro-anilino)acrylate | 10 | 5 | 5 | 5 | | | | | | 5- | 5- | 2 | | | | | | |
| Ethyl 2-cyano-3-(N-methyl-3-methyl-anilino)acrylate | 4 | 5 | 5 | 0 | | | | | | 2 | | 0 | 3+ | | | | | |
| Ethyl 2-cyano-3-(N-methyl-2-methyl-anilino)acrylate | 4 | 5 | 3+ | | | | | | | 5- | | 0 | 5 | | | | | |
| Ethyl 2-cyano-3-(N-methyl-4-hydroxy-anilino)acrylate | 25 | | 5- | | | | | | | | | 3+ | | | | 0 | 0 | |
| Ethyl 2-cyano-3-(N-methyl-4-methyl- | 25 | | 5- | | | | | | | | | 0 | | | 1 | 0 | | |

TABLE VI-continued

| Compound | Rate LB/Acre | LA | MU | PI | PU | CW | CG | GT | BA | CR | GRF | WO | MI | COR | RG | WH | RA | PA |
|---|---|---|---|---|---|---|---|---|---|---|---|---|---|---|---|---|---|---|
| anilino)acrylate Ethyl 2-cyano-3-methyl-3-anilino acrylate | 25 5 | 5– 4 | 5 | 5 | | | 0 | 5– | | | 0 | | 5– 5– | 5– | 4 | 5– | |
| Ethyl 2-cyano-3-(N-methyl-p-anisidino)-acrylate | 25 | 5 | | | | | | | | | | | 5 | 0 | 0 | 0 | | |
| Diethyl N-methyl-p-anisidino-methylenemalonate | 25 | 3 | | | | | | | | | | | 1 | 1 | 0 | 0 | | |
| N-methyl-p-anisidinomethylene-malononitrile | 25 | 3 | | | | | | | | | | | 3 | 0 | 0 | 0 | | |
| 1-anilinoethyl-idenemalononitrile | 25 | 4+ | | | | | | | | | | | 4+ | 4+ | 0 | 1 | | |
| 1-(p-anisidinoethyl-idenemalononitrile | 25 | 3 | | | | | | | | | | | 5– | 3 | 0 | 0 | | |
| 1-(4-chloro-anilino)methyl-idenemalononitrile | 25 | 5– | | | | | | | | | | | 5– | 0 | 0 | 0 | | |
| Diethyl anilinomethyl-enemalonate | 25 | 5– | 5 | | | | 5 | 4 | 5 | 5 | 1 | | 4+ | 0 | 1 | | | |

EXAMPLE 34

Selective Preemergence Herbicidal Activity

The selective preemergence herbicidal activity of the compounds of the present invention is demonstrated by the following tests in which ethyl 2-cyano-3-(N-methylanilino)acrylate dissolved in a 50/50 acetone/water solution was applied in dilute aqueous solution to seeded plots. The application was by standard spraying apparatus, operated so as to deliver 57 gal./acre of test solution which provides the equivalent of 2.0 or 3.0 lbs. of active ingredient/acre of seeded plot. The soil was prepared in the normal manner by plowing and harrowing. Seeds of the broadleaf weeds (i.e., pigweed, lambsquarters, smartweed, ragweed and jimpson weed) and grasses (i.e., foxtail and crabgrass) were broadcast over the plot and disked into the soil to assure heavy weed infestation. The plots, 5 ft. wide and 20 ft. long, were then planted with corn, soybeans, red beets, and sorghum in rows approximately 10 inches apart. When plantings were complete, the plots were uniformly sprayed with the test solution. Untreated control plots which were similarly planted are employed as controls. Twenty days after planting, the plots were examined and rated as to herbicidal activity according to the index given below. The control plots adjacent to test plots were heavily infested with all species of the broadleaf weeds and grasses employed in the tests. A value of 3 or less is acceptable for crop selectivity. The data obtained is presented in Table VII.

| HERBITOXICITY INDEX | |
|---|---|
| Numerical Scale | Herbicidal activity |
| 0 | No effect |
| 1 | 10% reduction in stand |
| 2 | 20% reduction in stand |
| 3 | 30% reduction in stand |
| 4 | 40% reduction in stand |
| 5 | 50% reduction in stand |
| 6 | 60% reduction in stand |
| 7 | 70% reduction in stand |
| 8 | 80% reduction in stand |
| 9 | 90% reduction in stand |
| 10 | 100% kill |

TABLE VII

| Rate Lb/Acre | Crops | | | Grasses | Broadleaf Weeds |
|---|---|---|---|---|---|
| | SG | SOY | COR | | |
| 2 | 0 | 0 | 0 | 9 | 7 |
| 3 | 3 | 0 | 0 | 10 | 9 |

EXAMPLE 35

Postemergence activity of the compounds of the invention is further demonstrated by the following tests wherein field plots planted to corn and soybeans and infested with carpet weed, dogfennel, lambsquarters, mustard, pigweed and millet approximately 6 to 18 inches high were sprayed with a 50/50 acetone/water mixture containing 0.1% of a surfactant and sufficient ethyl N-methylanilinomethylene cyanoacetate to provide the equivalent of one pound per acre of said compound. Thirty-four days after application the plots were examined and rated according to the index of Example 32. Data obtained is presented in Table VIII.

TABLE VIII

| Compound | Rate Lb/A | Weeds | | | | | | Crops | |
|---|---|---|---|---|---|---|---|---|---|
| | | CW | DG | LA | MU | PI | MI | COR | SOY |
| ethyl 2-cyano-3-(N-methylanilino)-acrylate | 1 | 9 | 9 | 8 | 9 | 9 | 0 | s | s |

I claim:

1. A method for the control of undesirable plant species comprising contacting said plant species with a herbicidally effective amount of a compound methyl 2-cyano-3-(N-methylanilino) acrylate, n-octyl 2-cyano-3-(N-methylanilino) acrylate, ethyl 2-cyano-3-(N-methyl-3-chloroanilino)acrylate, ethyl 2-cyano-3-(N-methyl-3-methylanilino)acrylate, ethyl 2-cyano-3-(N-methyl-2-methylanilino) acrylate or ethyl 3-(N-phenyl-N-methyl)-amino-2-cyano acrylate.

2. A method according to claim 1 wherein the compound is methyl 2-cyano-3-(N-methylanilino)acrylate.

3. A method according to claim 1 wherein the compound is n-octyl 2-cyano-3-(N-methylanilino)acrylate.

4. A method according to claim 1 wherein the compound is ethyl 2-cyano-3-(N-methyl-3-chloroanilino)acrylate.

5. A method according to claim 1 wherein the compound is ethyl 2-cyano-3-(N-methyl-3-methylanilino)acrylate.

6. A method according to claim 1 wherein the compound is ethyl 2-cyano-3-(N-methyl-2-methylanilino)acrylate.

7. A method for the preemergence control of undesirable plant species comprising applying to the soil containing the seeds of the undesirable plant species a herbicidally effective amount of a compound methyl 2-cyano-3-(N-methylanilino) acrylate, n-octyl 2-cyano-3-(N-methylanilino) acrylate, ethyl 2-cyano-3-(N-methyl-3-chloroanilino)acrylate, ethyl 2-cyano-3-(N-methyl-3-methylanilino)acrylate, ethyl 2-cyano-3-(N-methyl-2-methylanilino) acrylate or ethyl 3-(N-phenyl-N-methyl)-amino-2-cyano acrylate.

8. A method for the postemergence control of undesirable plant species comprising applying to the foliage of the undesirable plant species a herbicidally effective amount of a compound methyl 2-cyano-3-(N-methylanilino) acrylate, n-octyl 2-cyano-3-(N-methylanilino) acrylate, ethyl 2-cyano-3-(N-methyl-3-chloroanilino)acrylate, ethyl 2-cyano-3-(N-methyl-3-methylanilino)acrylate, ethyl 2-cyano-3-(N-methyl-2-methylanilino) acrylate or ethyl 3-(N-phenyl-N-methyl)-amino-2-cyano acrylate.

9. A process as claimed in claim 1, wherein said selective herbicide is ethyl $\beta$-(N-phenyl-N-methyl)-amino-$\alpha$-cyano acrylate.

* * * * *